US011923074B2

(12) United States Patent
Li et al.

(10) Patent No.: US 11,923,074 B2
(45) Date of Patent: Mar. 5, 2024

(54) PROFESSIONAL NETWORK-BASED IDENTIFICATION OF INFLUENTIAL THOUGHT LEADERS AND MEASUREMENT OF THEIR INFLUENCE VIA DEEP LEARNING

(71) Applicant: IQVIA Inc., Parsippany, NJ (US)

(72) Inventors: Ruoxin Li, Chapel Hill, NC (US);
Yong Cai, Plymouth Meeting, PA (US);
John H. Eichert, Jr., Doylestown, PA (US); Emily Zhao, Wayne, PA (US);
Yilian Yuan, North Wales, PA (US);
Yanping Liu, Harleysville, PA (US);
Steve Eichert, Jenkintown, PA (US); D. Bruce West, Doylestown, PA (US);
William McClellan, Havertown, PA (US)

(73) Assignee: IQVIA Inc., Parsippany, NJ (US)

( * ) Notice: Subject to any disclaimer, the term of this patent is extended or adjusted under 35 U.S.C. 154(b) by 293 days.

(21) Appl. No.: 17/174,705

(22) Filed: Feb. 12, 2021

(65) Prior Publication Data
US 2022/0262499 A1    Aug. 18, 2022

(51) Int. Cl.
*G16H 40/20*    (2018.01)
*G06N 3/045*    (2023.01)
*G06N 3/08*    (2023.01)

(52) U.S. Cl.
CPC .......... *G16H 40/20* (2018.01); *G06N 3/045* (2023.01); *G06N 3/08* (2013.01)

(58) Field of Classification Search
CPC ........ G16H 10/00–80/00; G06N 3/00–99/007; G06Q 10/00–2250/905
See application file for complete search history.

(56) References Cited

U.S. PATENT DOCUMENTS 8,224,684 B2 * 7/2012 Hawn .............. G06Q 10/06398
  705/7.29
10,475,045 B2 * 11/2019 Ferrarons Llagostera ...................
  G06F 16/24578
(Continued)

FOREIGN PATENT DOCUMENTS

CN    112329473 A  *  2/2021  ............. G06F 17/13
WO   WO-2010065111 A1 *  6/2010  ............. G06F 16/23

OTHER PUBLICATIONS

Keating et al., "Association of Physician Peer Influence With Subsequent Physician Adoption and Use of Bevacizumab," JAMA Network Open. 2020;3(1):e1918586. doi:10.1001/jamanetworkopen. 2019.18586. (Year: 2020).*
(Continued)

*Primary Examiner* — Jonathon A. Szumny
(74) *Attorney, Agent, or Firm* — Fish & Richardson P.C.

(57) ABSTRACT

Embodiments of the present disclosure provide a method for identifying those entities within a network that have the most influence on other entities within the network. A multi-relational network comprising links among a plurality of physicians is generated based on peer network data, wherein each link indicates a first physician that influences a second physician, and a weight of the influence. A decision by a treating physician of the plurality of physicians is decomposed, using a deep learning engine, into a magnitude of peer influence and a magnitude of control factor influence based on the multi-relational network and a plurality of control factors respectively. The magnitude of peer influence among one or more physicians in the multi-relational network is distributed among physicians in the multi-relational network based on the links each physician maintains with other physicians.

20 Claims, 7 Drawing Sheets

(56) References Cited

U.S. PATENT DOCUMENTS

| | | | | |
|---|---|---|---|---|
| 11,238,123 B1* | 2/2022 | Wang | | G06F 16/9536 |
| 11,436,291 B1* | 9/2022 | Tayeb | | G06F 16/9536 |
| 2005/0075922 A1* | 4/2005 | Brady | | G06Q 30/02 |
| | | | | 705/7.29 |
| 2006/0042483 A1* | 3/2006 | Work | | G06Q 10/00 |
| | | | | 101/91 |
| 2010/0268574 A1* | 10/2010 | Butcher | | G06Q 10/10 |
| | | | | 709/224 |
| 2012/0179002 A1* | 7/2012 | Brunetti | | G16H 20/00 |
| | | | | 600/300 |
| 2012/0209832 A1* | 8/2012 | Neystadt | | G06Q 50/01 |
| | | | | 707/723 |
| 2013/0254280 A1* | 9/2013 | Yang | | G06Q 30/0251 |
| | | | | 709/204 |
| 2014/0089323 A1* | 3/2014 | Wu | | G06Q 50/01 |
| | | | | 707/748 |
| 2014/0372523 A1* | 12/2014 | Hande | | G06Q 50/01 |
| | | | | 709/204 |
| 2015/0007037 A1* | 1/2015 | Butler | | G06Q 10/10 |
| | | | | 715/736 |
| 2015/0120717 A1* | 4/2015 | Kim | | G06F 16/335 |
| | | | | 707/727 |
| 2015/0170295 A1* | 6/2015 | Shen | | G06Q 50/01 |
| | | | | 705/319 |
| 2016/0028614 A1* | 1/2016 | Kumar | | H04L 45/122 |
| | | | | 370/254 |
| 2016/0283884 A1* | 9/2016 | Wilson | | G06Q 50/01 |
| 2017/0262451 A1* | 9/2017 | Milner | | G06F 16/285 |
| 2017/0330357 A1* | 11/2017 | Siegel | | G06F 16/248 |
| 2018/0196813 A1* | 7/2018 | Lin | | G06Q 50/01 |
| 2018/0341710 A1* | 11/2018 | Liang | | G06Q 20/384 |
| 2022/0138651 A1* | 5/2022 | Ramaswamy | ... | G06Q 10/06311 |
| | | | | 705/7.13 |
| 2022/0261546 A1* | 8/2022 | Liu | | G06F 40/30 |

OTHER PUBLICATIONS

Keating et al., "Factors Affecting Influential Discussions Among Physicians: A Social Network Analysis of a Primary Care Practice," Society of General Internal Medicine 2007;22:794-798; DOI: 10.1007/s11606-007-0190-8. (Year: 2007).*

Donohue et al., "Influence of peer networks on physician adoption of new drugs," PLoS One 13(10): e0204826. (Year: 2018).*

Ramesh et al., "Multi-relational Influence Models for Online Professional Networks," ACM. 978-1-4503-4951-2/17/08; DOI: 10.1145/3106426.3106531. (Year: 2017).*

Thomas W. Valente, "Social network thresholds in the diffusion of innovations," Social Networks 18(1996) 69-89. (Year: 1996).*

Backstrom et al., "Supervised Random Walks: Predicting and Recommending Links in Social Networks," WSDM'11, Feb. 9-12, 2011, Hong Kong, China; Copyright 2011 ACM 978-1-4503-0493-1/11/02. (Year: 2011).*

* cited by examiner

PROFESSIONAL NETWORK-BASED IDENTIFICATION OF INFLUENTIAL THOUGHT LEADERS AND MEASUREMENT OF THEIR INFLUENCE VIA DEEP LEARNING

TECHNICAL FIELD

Aspects of the present disclosure relate to implementation of machine learning techniques to identify those entities within a network that have influence on other entities within the network and accurately measure the influence reflected in the adoption of new therapies.

BACKGROUND

Thought leaders are essential components for network marketing efforts designed to drive the awareness and diffusion of new science, as well as the adoption of new products. This is because thought leaders have a disproportionate impact/influence on others within their industry with respect to industry narratives (establishing science etc.). With respect to the influence such thought leaders have, a large part of their market impact is attributable to the behavioral influence these thought leaders have on the decisions of their peers.

BRIEF DESCRIPTION OF THE DRAWINGS

The described embodiments and the advantages thereof may best be understood by referring to the following description in conjunction with the accompanying drawings. These drawings in no way limit any changes in form and detail that may be made to the described embodiments by one skilled in the art without departing from the spirit and scope of the described embodiments.

DETAILED DESCRIPTION

Although thought leaders have a disproportionate impact/influence on others within their industry with respect to industry narratives, traditional communication and marketing strategies generally focuses on value derived through e.g., early adopting and self-prescribing, despite social contagion and innovation diffusion being important factors that drive product success. For instance, in the medical industry, when attempting to identify the most influential physicians for achieving optimal market share, it is important to assess their indirect, peer influence in addition to the self-prescribing, new-to-brand (NBRx) metric. However, while NBRx is directly observable (based on prescriptions written etc.), peer influence is difficult to directly observe. Instead, peer influence is embedded in the physician's prescribing activities as well as their interactions with each other in various professional activities, relationships, and peer networks for example.

Current techniques for measuring peer influence either rely on measuring an early adopter's own prescribing behavior or use network centrality as a proxy for peer influence. These techniques either miss the influence measures or are incomplete in measuring them. In addition, current techniques address a portion of the business questions that pertain to measuring adoption of new therapies, and thus multiple methodologies are required to get a picture of influence at local level (i.e., any one method by itself is incomplete picture). Such fragmented analytic approaches may be disjointed and not aligned. Thus, even when hypothetically combined, they still lack the ability to completely capture leader-follower connections and to quantify peer influence in terms of sales. Further, such methods are unable to determine how/where influence occurs. In addition, the quantification methodology of such approaches is often assumption-based, rather than evidence-based.

The present disclosure addresses the above-noted and other deficiencies by using artificial intelligence (AI)/machine learning (ML), social network analytics, big data analytics, etc. to seamlessly integrate factors relevant to peer influence and obtain a holistic picture of peer-to-peer dynamics. The embodiments described herein may utilize raw peer network data to establish a physician (also referred to herein as "health care provider" or, "HCP") peer network and measure the diffusion of adoption of new therapies across the peer network. The embodiments described herein may also utilize a large amount of health care data to account for a variety of control factors that can also influence the diffusion of adoption of new therapies across the peer network. The results may indicate thought leaders in the peer network and their followers (e.g., those they influence), as well as measure the impact of such thought leaders (e.g., early adopters of a new drug) on the prescribing behavior of other physicians in their peer network that they influence (e.g., what level of influence do thought leaders have on whether other physicians they influence in the peer network will adopt the new drug?). Thus, embodiments of the present disclosure address the technical problem of refining and analyzing large amounts of raw healthcare and peer network data in such a way that influential physicians in a network and their level of influence on others may be identified. Although discussed with respect to determining peer influence among physicians for purposes of illustration, it should be noted that the embodiments described herein may be applied to determining peer influence in a variety of fields (e.g., engineering, law, finance, economics).

In one example, a method for determining which physicians in a peer network have the most peer influence is provided. The method comprises generating a multi-relational network comprising links among a plurality of physicians based on peer network data. Our peer network included routine discussion among near peers, expert clinical advice provided by a colleague, recognition as a prominent national expert, and perception of being a future thought leader. In addition, we establish peer networks using referral and shared patient data, as well as early adopter-follower Rx analysis. Each link in the network indicates a first physician that influences a second physician, and a weight of the influence. The method additionally comprises quantifying, using a deep learning engine, the peer influence of a decision made by a treating physician, wherein the quantification is controlled by a set of environmental factors and a set of patient factors. The method may further comprise distributing the peer influence among one or more physicians in the multi-relational network based on the links each physician maintains with other physicians.

In another example, a system for determining which entities in a peer network have the most peer influence is provided. The system may comprise a memory and a processing device operatively coupled to the memory. The processing device may generate a multi-relational network comprising links among a plurality of entities based on peer network data, wherein each link indicates a first entity that influences a second entity, and a weight of the influence. The processing device may additionally decompose, using a deep learning engine, a decision by an acting entity of the plurality of entities into a magnitude of peer influence and a magnitude of control factor influence based on the multi-relational network and a plurality of control factors respectively, wherein the plurality of control factors includes a set of environmental factors and a set of subject factors. The method may further comprise distributing the magnitude of peer influence among one or more entities in the multi-relational network based on the links each entity maintains with other entities.

Figure 1:
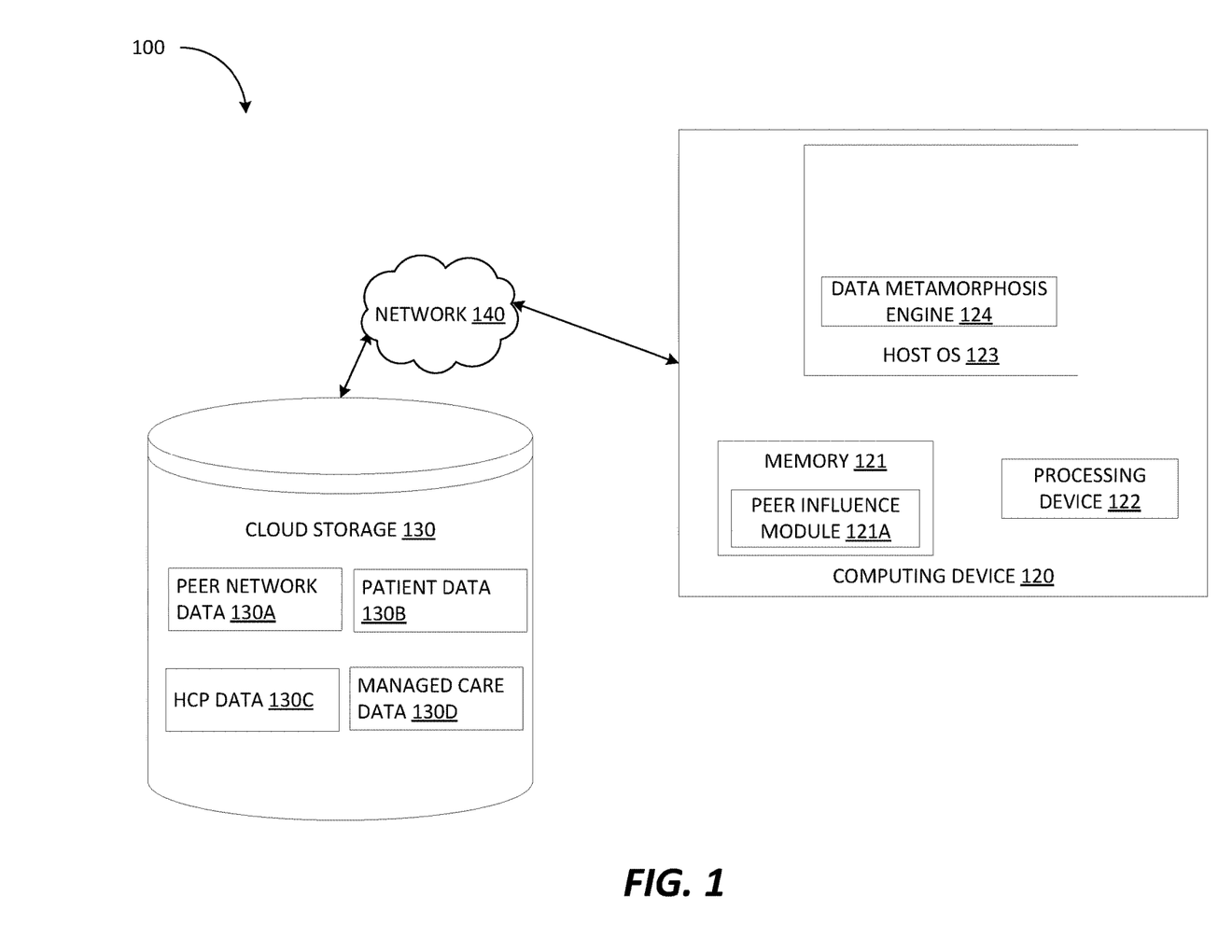
FIG. 1 is a block diagram that illustrates an example cloud system, in accordance with some embodiments of the present disclosure.

FIG. 1 is a block diagram that illustrates an example cloud system 100. As illustrated in FIG. 1, the cloud system 100 includes a computing device 120, a cloud storage 130 and a network 140. The computing device 120 and the cloud storage 130 may be coupled to each other (e.g., may be operatively coupled, communicatively coupled, may communicate data/messages with each other) via network 140. Network 140 may be a public network (e.g., the internet), a private network (e.g., a local area network (LAN) or wide area network (WAN)), or a combination thereof. In one embodiment, network 140 may include a wired or a wireless infrastructure, which may be provided by one or more wireless communications systems, such as a WiFi™ hotspot connected with the network 140 and/or a wireless carrier system that can be implemented using various data processing equipment, communication towers (e.g. cell towers), etc. The network 140 may carry communications (e.g., data, message, packets, frames, etc.) between computing device 120 and cloud storage 130. The computing device 120 (and cloud storage 130) may include hardware such as processing devices (e.g., processors, central processing units (CPUs)), memory (e.g., random access memory (RAM), storage devices (e.g., hard-disk drive (HDD)), and solid-state drives (SSD), etc.), and other hardware devices (e.g., sound card, video card, etc.). A storage device may comprise a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices.

FIG. 1 and the other figures may use like reference numerals to identify like elements. A letter after a reference numeral, such as "110A," indicates that the text refers specifically to the element having that particular reference numeral. A reference numeral in the text without a following letter, such as "110," refers to any or all of the elements in the figures bearing that reference numeral.

The computing device 120 and cloud storage 130 may each comprise any suitable type of computing device or machine that has a programmable processor including, for example, server computers, desktop computers, laptop computers, tablet computers, smartphones, set-top boxes, etc. In some examples, the computing device 120 and cloud storage 130 may comprise a single machine or may include multiple interconnected machines (e.g., multiple servers configured in a cluster) that are all located at the same or different geographic region. The computing device 120 and cloud storage 130 may be implemented by a common entity/organization or may be implemented by different entities/organizations. For example, computing device 120 may be operated by a first company/corporation and cloud storage 130 may be operated by a second company/corporation. The computing device 120 and cloud storage 130 may each execute or include an operating system (OS), as discussed in more detail below. The OSs of computing device 120 and cloud storage 130 may manage the execution of other components (e.g., software, applications, etc.) and/or may manage access to the hardware (e.g., processors, memory, storage devices etc.) of the computing device.

Cloud storage 130 may comprise a plurality of persistent storage devices that provide large-scale and high density data storage which may be virtualized into logical pools and provided to clients (e.g., over network 140) as e.g., object storage. Object storage is a computer data storage architecture that manages data as objects, where each object typically includes the data itself, a variable amount of metadata, and a globally unique identifier. In this way, clients can perform selective extraction and analysis of data. As shown in FIG. 1, cloud storage 130 may include peer network data 130A that may indicate links between physicians. The peer network data 130A may include peer nomination surveys, publication co-authors, conference speakers and participants, referral network data, social network data, shared patients, and data from affiliation networks (e.g., Sunshine, Onekey™), for example. Cloud storage 130 may also include patient data 130B such as patient sequential medical histories (not limited to brand and market definition), demographics, and medical/out of pocket treatment cost for example, for a plurality of patients. Cloud storage 130 may further include health care provider (HCP) data 130C such as physician characteristics, prescribing preferences, promotions, and demographics, for example. Cloud storage 130 may further include managed care data 130D such as payer/plan copay rates, rejection, reversal, and copay differential, for example.

Such data may be sourced from claims and patient data, hospitals, registries, healthcare providers, government/third party databases and other groups anywhere in the world which may form part of a connected network infrastructure for obtaining healthcare data. Although discussed with respect to healthcare data for purposes of illustration, it should be noted that the embodiments described herein may be applied in a variety of fields (e.g., engineering, law, finance, economics).

Computing device 120 may implement a data metamorphosis engine 124 that may integrate, enrich, and transform data from cloud storage 130 (which includes raw data from many disparate data sources) into integrated data at scale for advanced analytics, machine learning, and AI/ML, applications, for example.

Figure 2:
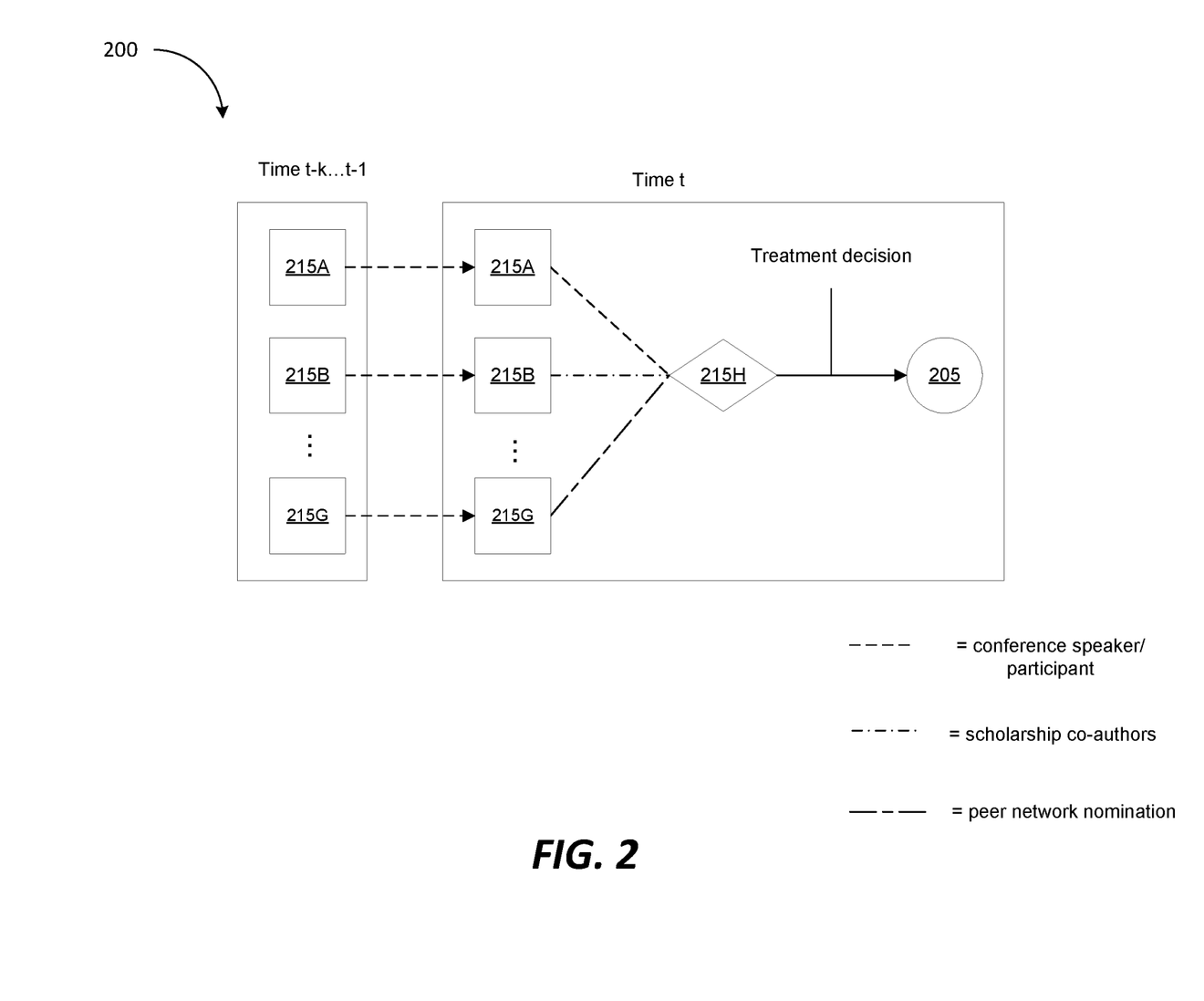
FIG. 2 is a block diagram that illustrates a schematic of a peer network in which peer influence can be measured, in accordance with some embodiments of the present disclosure.

FIG. 2 illustrates a schematic diagram of a physician network 200 in which the influence of physicians in the network on each other (peer influence) can be measured by embodiments of the present disclosure. At time t, a patient 205 sees a treating physician 215H who has not been adopting the new drug yet. This treating physician 215H may be connected with peers 215A-N through various network links (indicated with dashed lines in FIG. 2) such as social networks, referrals, peer nominations, or advice ties, for example. It should be noted that 2 physicians may be linked by multiple network links. Peer 215A may be an early adopter of the drug, while peers 215B and G may be physicians who have not adopted the new drug yet. A physician peer 215's early adoption status at time t is determined by the prior period from t-k up to t-1 (using e.g., IQVIA claims data). In an empirical use case, we may set k=6 months, for example, which can be parametrized. The objective is to measure how much physician 215H's treatment decision is influenced by connections to early adopters (e.g., peer 215A) as well as the influence strength by network link types (e.g., article co-authors, peer referral). Although illustrated with only 3 peer physicians 215 for simplicity of illustration, treating physician 215H may have any appropriate number of peer physicians in his/her network and may maintain any type of connection with each of the peer physicians such as shared patients, referrals, network affiliations etc.

Referring also to FIG. 1, computing device 120 may (via processing device 122) execute peer influence module 121A to perform the embodiments described herein. For example, in response to determining that the treating physician 215H (who previously was not an adopter of a particular drug (referred to herein as "drug X")) has prescribed drug X to a patient, computing device 120 may execute the peer influence module 121A to determine the effect of physician network 200 on treating physician 215H's decision to prescribe drug X. Upon execution, computing device 120 may generate a multi-relational network indicating links between physicians 215 in physician network 200. More specifically, computing device 120 may establish links (pair relationships) between physicians 215 using the peer network data 130A from cloud storage 130. Each link may indicate a pair of physicians 215 that are connected and how they are connected. Computing device 120 may determine pairs based on e.g., peer nomination surveys, publication co-authors, conference speakers and participants, referral networks, social networks, shared patients, professional organization memberships, and affiliation networks (e.g., Onekey™), included within the peer network data 130A. Each link between two physicians 215 may also indicate which of the physicians in the pair influences the other, and a weight of that influence may be assigned to the link. The weight of the influence of a link may be based upon the type of connection between the two physicians 215 (e.g., publication co-authors, conference speakers and participants) and may be determined using model 300 as described in further detail herein with respect to FIG. 3. Upon determining all of the links/pair relationships between physicians 215 in the network 200, a complete multi-relational network 400 may result (illustrated in FIGS. 4A and 4B), which may be represented and stored as multi-relational network data 320 (shown in FIG. 3). The multi-relational network 400 may be represented as a tree structure as shown in FIGS. 4A and 4B. FIG. 4A illustrates the flow of influence among physicians 215 throughout the network 400 as discussed in further detail herein. One or more of the links in multi-relational network 400 may have a different impact in the overall decision making process that treating physician 215H may go through when deciding to write a prescription for drug X which they have never prescribed before, as discussed in further detail herein.

In some embodiments, certain links may be missing because there is insufficient information to ascertain the links. In such cases, computing device 120 may build link prediction models to complete the links between physicians when they are missing. Computing device 120 may perform link prediction using predictive analytics in situations where, for example, a peer physician did not participate in a survey, or their referrals are not captured in the peer network data 130A, so that their influence may not be directly measurable.

Determining the physicians in the multi-relational network 400 who have the most influential opinions is difficult because the power of peer influence is not easily observable. While a person can easily observe the influence of self-prescribing (i.e. early adoption), the influential power of peer physicians is not easily observable, especially with complex multi-relational network structures (different ties, relationships, etc.). As a result, computing device 120 may utilize causal modeling to measure the peer influence of the multi-relational network 400 as a whole.

Figure 3:
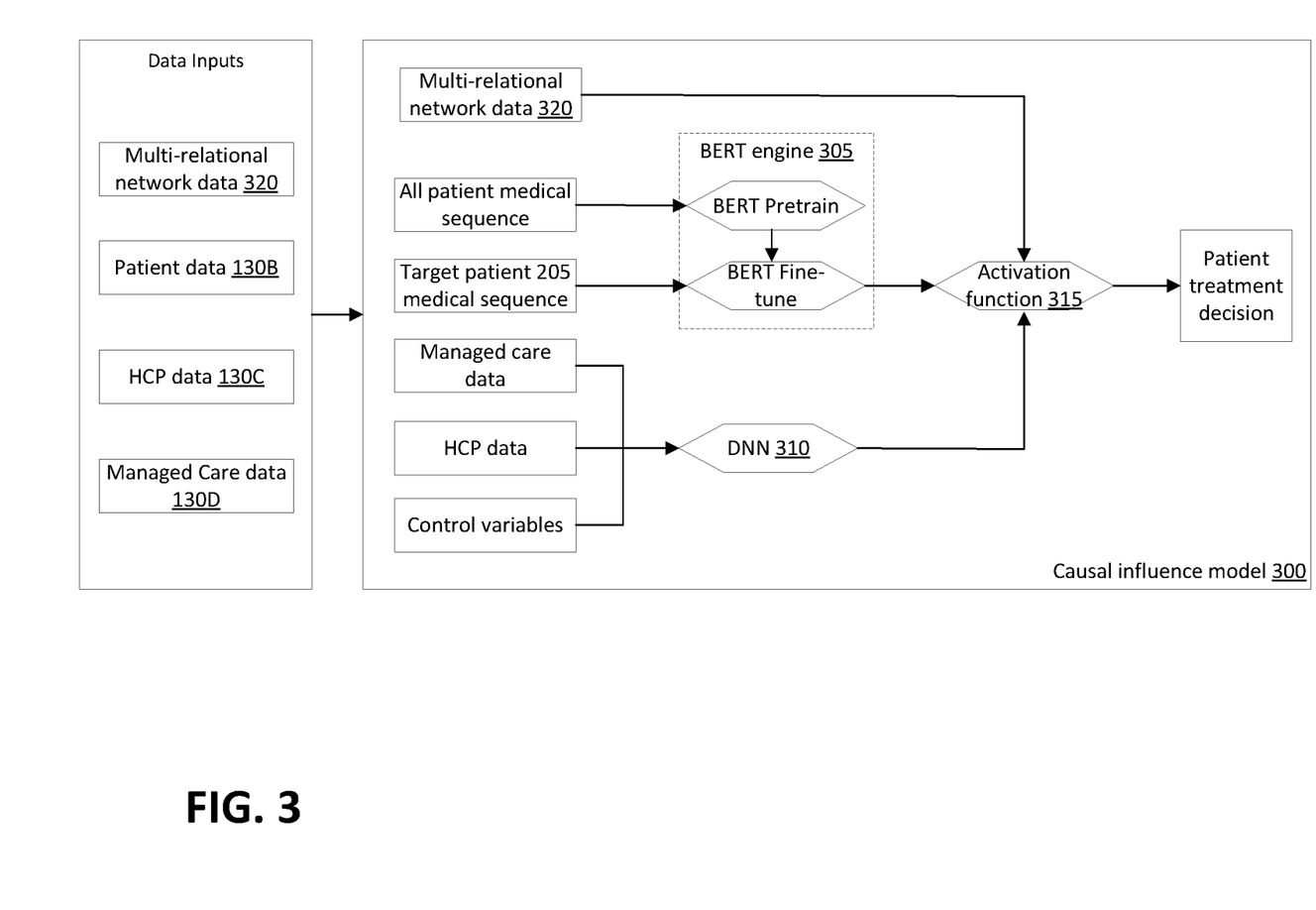
FIG. 3 is a block diagram of a machine learning model that decomposes a treatment decision into peer influence and control factor influence, in accordance with some embodiments of the present disclosure.
Figure 4A:
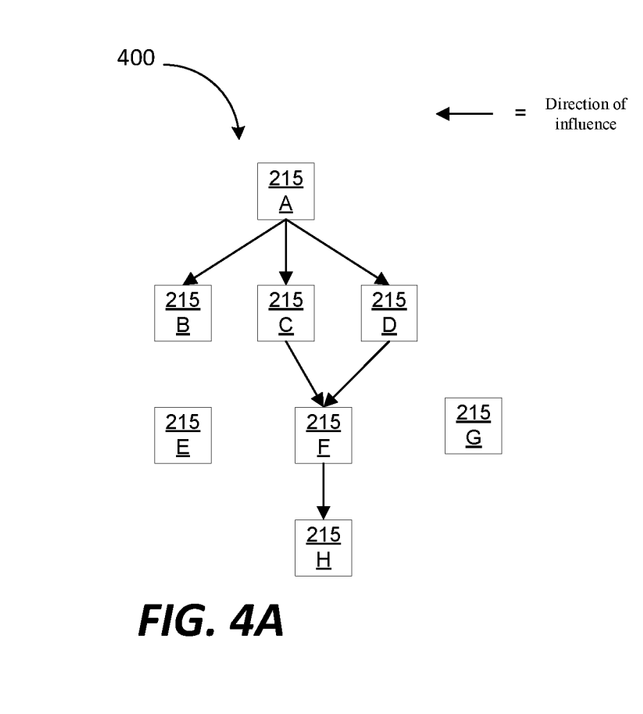
FIG. 4A is a tree diagram illustrating the direction of influence among physicians in a network, in accordance with some embodiments of the present disclosure.
Figure 4B:
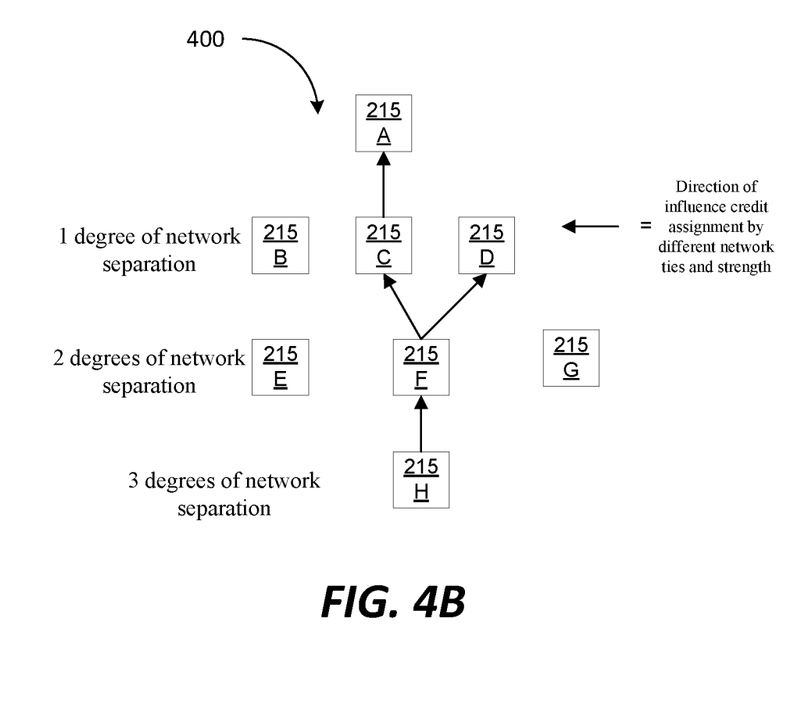
FIG. 4B is a tree diagram illustrating the direction of influence credit distribution among physicians in a network, in accordance with some embodiments of the present disclosure.

FIG. 3 illustrates a causal influence model 300, which may be a deep learning model and may be used by the computing device 120 to measure the magnitude of peer influence (e.g., from peer physicians 215 in physician network 200—represented by multi-relational network 400) on the treating physician 215H's treatment decision.

In order to measure the peer influence of the network 400, a physician's treatment decision must be decomposed into base components, so as to account for a variety of control factors, and identify the magnitude of influence of the peer network (multi-relational network) from the magnitude of influence of the control factors. The influence of the multi-relational network 400 may also be referred to as the causal influence. Data inputs to the model 300 may include the multi-relational network data 320, which may be the primary factor from which the influence of the multi-relational network 400 may be determined, as well as the patient data 130B, the health care provider (HCP) data 130C, and the managed care data 130D, for example. The patient data 130B, health care provider (HCP) data 130C, and managed care data 130D may be examples of data that represents control factors, which are factors other than the peer network that also influence the treating physician 215H's treatment decision. In the example of FIG. 3, the control factors may include patient factors (represented by the patient data 130B) and environmental factors (represented by the HCP data 130C and the managed care data 130D), as discussed in further detail herein.

The model 300 may comprise a deep learning engine comprises a Bidirectional Encoder Representations from Transformers (BERT) engine 305, deep neural networks (DNN) 310, and an activation function 315.

The DNN 310's function is to parse out the magnitude of the influence that environmental factors have in physician 215H's treatment decision. Stated differently, the DNN 310 allows the model 300 to control for environmental factors such as characteristics of the treating physician 215H (e.g., graduation year, board membership, years in practice, number of similar procedures they have done, etc.), prescribing preferences, promotions (e.g., promotional material sent to and face-to-face calls with treating physician 215H etc.), and demographics, for example (all of which may be derived from HCP data 130C). The DNN 310 may also allow the model 300 to control for environmental factors such as payer/plan copay rates, rejection, reversal, and copay differential (derived from managed care data 130D). For example, the DNN 310 may allow the model 300 to determine the influence on treating physician 215H's treatment decision of factors such as whether physician 215H is a prescribing doctor who can perform this treatment, whether the patient 205's healthcare plan allow for this kind of treatment, and whether there a rejection rate low enough that allows this treatment to be effective. The DNN 310 allows the model 300 to account for the magnitude of influence that environmental factors have on treating physician 215H's decision, and allows the model 300 to single out the influence of the peer network (which is also referred to as the causal influence) as discussed herein.

The BERT engine 305 may leverage a sequence model to train on patient longitudinal data (patient data 130B) such as patient sequential medical histories (indicating the effect of varying medical conditions among different patients), demographics, and medical/out of pocket treatment cost, for a large sample number of patients. In this way, the BERT engine 305 allows the model 300 to control for factors specific to the patient 205 (i.e., parse out the magnitude of influence that patient factors specific to patient 205 have on treating physician 215H's treatment decision). A patient's medical condition may be difficult to control for. This is because diagnosis and treatment often occur over months and years, some conditions advance over time, and there are tens of thousands of diagnosis codes. In addition, there can be millions of patient records. As a result, patient medical data can form a large and complex data structure with potentially tens of thousands of dimensions, which cannot be easily processed by the activation function 315. However, the BERT engine 305 may account for sequential information such as medical condition progress over time, and may project complex data structures with tens of millions of dimensions into a smaller dimension space (e.g., from 10,000,000 dimensions to 300) via a process referred to as embedding. When the BERT engine 305 projects a large and complex data (e.g., 10,000,000 dimensions) structure into a smaller dimension space, it may maintain the majority of the data from the 10,000,000 dimensions, thereby providing a dimension reduction mechanism. The BERT engine 305 allows the model 300 to account for the magnitude of influence that patient factors specific to patient 205 have on treating physician 215H's decision, and allows the model 300 to single out the influence of the peer network (which is also referred to as the causal influence) as discussed herein.

The magnitude of the multi-relational network 400's influence (causal effect) may be derived from the multi-relational network data 320. Activation function 315 may jointly model the magnitude of influence of the multi-relational network 400, the patient factors, and the environmental factors and allows the model 300 to predict what kind of treatment decision the treating physician 215H is going to make. As discussed herein, the major factor is multi-relational network data 320, while all other factors may act as control factors. The output of the model 300 may be a treatment decision (e.g., treating physician 215H prescribed drug X), and the decomposition of what influenced the decision (e.g., 10% came from promotional material, 30% came from peer influence owing to multi-relational network 400). The magnitude of peer influence owing to multi-relational network 400 may also be decomposed into a magnitude of influence of each link in the multi-relational network 400. In some embodiments, an automation pipeline connects data from cloud storage 130 to optimize the efficiency of the model 300. More specifically, an automation pipeline can automatically integrate and transform the complex relational data from cloud storage 130 into a format that the deep learning engine 300 may take as inputs. The automation pipeline also searches the best combination of hyper-parameters that minimizes the predication error. Without the pipeline, manual tuning would be extremely time consuming.

After utilising the causal influence model 300 to measure the magnitude of the influence from the multi-relational network 400 (which represents the physician network 200), computing device 120 may distribute that magnitude among physicians 215A-G in the multi-relational network 400. Computing device 120 may utilize an influence attribution algorithm to perform a bottom up traversal analysis of the multi-relational network 400 and determine what portion of the peer influence magnitude should be assigned to each physician 215A-G at each level of the multi-relational network 400 through n-degrees of network separation to appropriately distribute the influence magnitude among physicians in the multi-relational network 400. The influence attribution algorithm may comprise a depth-first tree search algorithm, or any other appropriate algorithm. FIG. 4A illustrates the multi-relational network 400, with physicians 215A-H organized into a tree structure based on their respective links and corresponding influence weights and indicates the direction of influence (as opposed to influence credit) from top down with arrows pointing from physicians to the physicians that they influence. Treating physician 215H may be located at the bottom of the tree structure. In the example of FIG. 4A, physician A influences physicians B, C and D directly (and physicians F and H indirectly); both physicians C and D influence physician F directly (and physician H indirectly); and physician F directly influences physician H as indicated by the arrow pointing from physician F to physician H.

FIG. 4B illustrates the multi-relational network 400, illustrating the direction of influence credit with arrows pointing from physicians to the physicians who influence them and who will receive a portion of influence credit. Stated differently, FIG. 4B indicates the direction in which influence credit is distributed with arrows pointing from physicians who are influenced to physicians that influence them and are thus receiving a portion of the magnitude value of the influence of multi-relational network 400.

In response to physician H writing a prescription for drug X, the causal model 300 may decompose physician H's treatment decision to determine the magnitude of the influence of the multi-relational network 400 on the treatment decision as well as the magnitude of other control factors (e.g., managed care environment, HCP demographics, and promotional activities), as discussed herein. In order to distribute the magnitude of the influence of the multi-relational network 400, computing device 120 may utilize an influence attribution algorithm to determine how the magnitude of the influence of the multi-relational network 400 should be distributed among the physicians 215A-G in multi-relational network 400 as follows. More specifically, computing device 120 (executing the depth-first search algorithm) finds the physician that wrote the prescription, in this case physician 215H at the bottom of the tree and may calculate an influence score based on the magnitude of the influence of network 400 (using the output of the causal influence model 300). Computing device 120 may distribute the influence score to physicians 215 in the next level of the network 400 that influence physician 215H, based on their influence weight as determined by the computing device 120 when generating the multi-relational network 400. In the example of FIG. 4B, physician F is the only physician in the next level that influences physician H, and so the influence score may be distributed to physician F based on the weight of physician F's influence on physician H. Computing device 120 may then iterate this process until it reaches the top of the tree.

In the example of FIG. 4B, physician 215F may have an influence weight of 0.1, while physicians 215C and D each have an influence weight of 0.2 on physician 215F, and physician 215A may have an influence weight of 0.5 on each of physician 215 B, C, and D. Thus, if the initial influence score is calculated to be 100, then 10 may be assigned to physician 215F as physician 215F's influence weight is 0.1. Then, the influence score of 100 is distributed to the influencers of physician 215F, which are physicians 215C and D. Each of physicians 215C and D may receive an influence score of 20 as their influence weight is 0.2 (higher than physician 215F's). The influence of 100 may again be distributed to the influencers of physicians 215C and D, which is physician 215A, who has the highest influence weighting of 0.5. Thus, physician 215A may receive an influence score of 50. As can be seen by the example of FIG. 4B, the total influence score of physician A is the sum of all subsequent peer influence scores below her. As can be seen, the final influence score for a physician 215 attenuates as the degree-of-separation between that physician and physician 215A increases. In this way, every physician 215 in the multi-relational network 400 is assigned their share of the magnitude value of the influence of multi-relational network 400 based on their individual influence in the network 400.

The computing device 120 may output the assigned score for each physician 215 in the network 400. Thus, each physician 215 may have a self-prescription score (determined as known in the art) and a peer influence score (determined using embodiments of the present disclosure). These scores may be combined to provide a total score, which may allow a number of different analyses to be performed. For example, physicians 215 may be segmented into buckets (e.g., high, medium, low influence). In essence, by understanding their total values, the optimization of marketing strategies for each physician 215 can be performed. The techniques described herein may allow health care companies to gain insights of a physician 215's role in new product diffusion and enable brand teams to compare network values and tradeoff market research decisions (e.g., targeting, segmentation, multichannel marketing optimization, etc), for example.

As discussed above, although described with respect to identifying influential physicians in a peer network of physicians, the embodiments described herein may be used generally to identify influential entities in a network of entities. For example, the computing device 120 may generate a multi-relational network comprising links among a plurality of entities based on peer network data, wherein each link indicates a first entity that influences a second entity, and a weight of the influence. Computing device 120 may additionally decompose, using a deep learning engine, a decision by an acting entity (e.g., the entity that has taken some action, and whose decision to do so we wish to decompose into component parts to learn what influenced the decision) of the plurality of entities into a magnitude of peer influence and a magnitude of control factor influence based on the multi-relational network and a plurality of control factors respectively, wherein the plurality of control factors includes a set of environmental factors and a set of subject factors. The set of subject factors may relate to factors about the subject of the action taken by the acting entity (i.e., the subject that was acted upon). Computing device 120 may further distribute the magnitude of peer influence among one or more entities in the multi-relational network based on the links each entity maintains with other entities.

Figure 5:
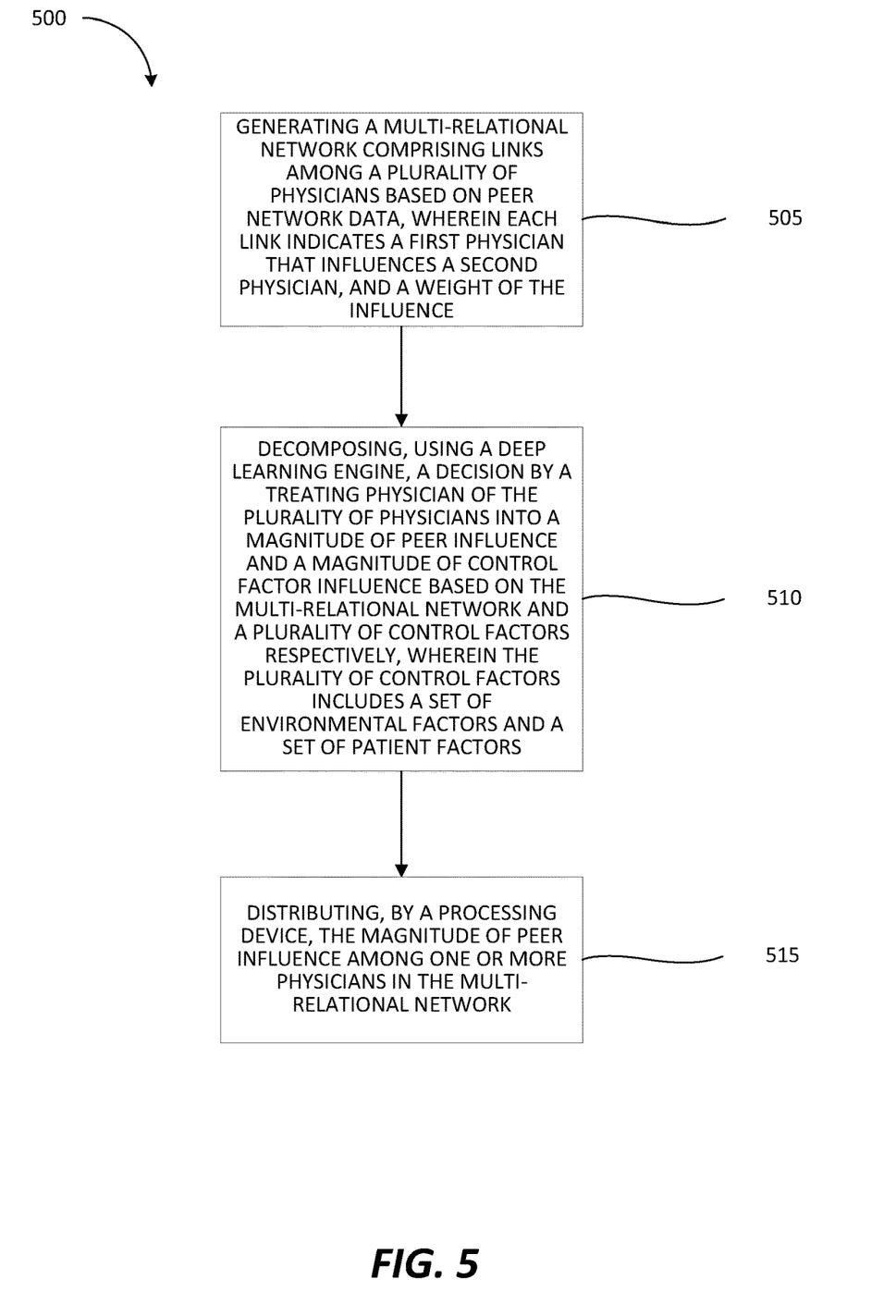
FIG. 5 is a flow diagram of a method for determining which physicians in a peer network have the most peer influence, in accordance with some embodiments of the present disclosure.

FIG. 5 is a flow diagram of a method 500 of determining which physicians in a peer network have the most peer influence, in accordance with some embodiments of the present disclosure. Method 500 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 500 may be performed by a computing device (e.g., computing device 120 illustrated in FIG. 1).

Referring simultaneously to FIGS. 1 and 2, the method 500 begins at block 505, where computing device 120 may generate a multi-relational network comprising links among a plurality of physicians based on peer network data, wherein each link indicates a first physician 215 that influences a second physician 215, and a weight of the influence. More specifically, computing device 120 may establish links (pair relationships) between physicians 215 using the peer network data 130A from cloud storage 130. Each link may indicate a pair of physicians 215 that are connected and how they are connected. Computing device 120 may determine pairs based on peer nomination surveys, publication co-authors, conference speakers and participants, referral networks, social networks, shared patients, and affiliation networks (e.g., Sunshine, Onekey™), included within the peer network data 130A. Each link between 2 physicians 215 may also indicate which of the physicians in the pair influences the other, and a weight of that influence. The weight of the influence may be based upon the type of connection between the 2 physicians 215 (e.g., publication co-authors, conference speakers and participants). Upon determining all of the links/pair relationships between physicians 215 in the network 200, a complete multi-relational network 400 may result (illustrated in FIGS. 4A and 4B), which may be represented and stored as multi-relational network data 320 (shown in FIG. 3). The multi-relational network 400 may be represented as a tree structure as shown in FIGS. 4A and 4B. FIG. 4A illustrates the flow of influence among physicians 215 throughout the network 400 as discussed in further detail herein. One or more of these links may have a different impact in the overall decision making process that treating physician 215H may go through when deciding to write a prescription for drug X which they have never prescribed before, as discussed in further detail herein.

At block 510, the computing device may decompose, using a deep learning engine, a decision by a treating physician of the plurality of physicians into a magnitude of peer influence and a magnitude of control factor influence based on the multi-relational network and a plurality of control factors respectively, wherein the plurality of control factors includes a set of environmental factors and a set of patient factors.

Figure 6:
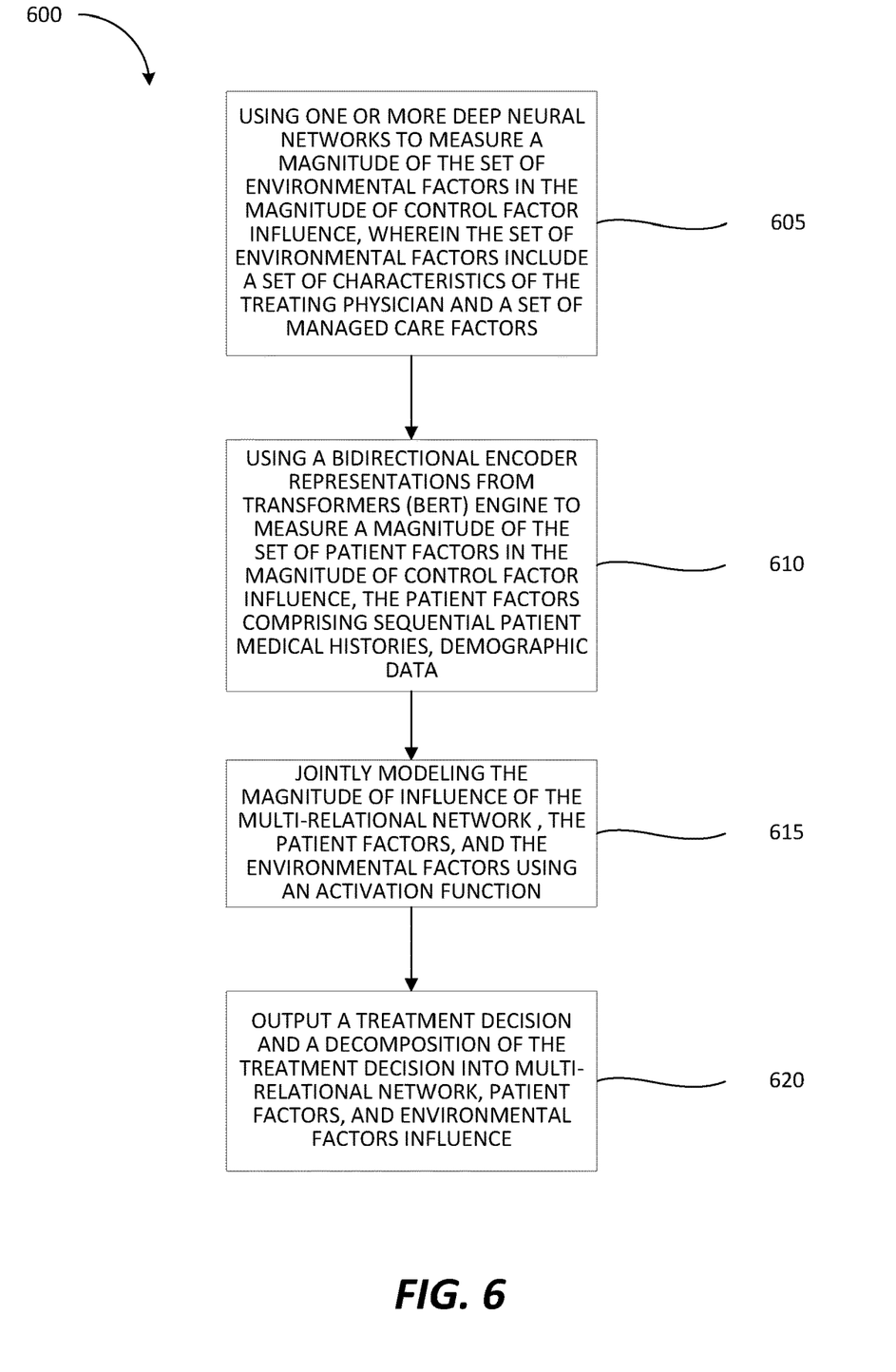
FIG. 6 is a flow diagram of a method for distributing a magnitude of a peer network influence among physicians in the peer network, in accordance with some embodiments of the present disclosure.

FIG. 6 is a flow diagram of a method 500 for distributing a magnitude of a peer network influence among physicians in the peer network, in accordance with some embodiments of the present disclosure. Method 600 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 600 may be performed by a computing device (e.g., computing device 120 illustrated in FIG. 1).

Referring also to FIGS. 1 and 2, in order to measure the peer influence of the network 400, a physician's treatment decision must be decomposed into base components, so as to account for a variety of control factors, and single out the magnitude of influence of the peer network (multi-relational network) from the magnitude of influence of the control factors. The influence of the multi-relational network 400 may also be referred to as the causal influence. Data inputs to the model 300 may include the multi-relational network data 320, which may be the primary factor from which the influence of the multi-relational network 400 may be determined, as well as the patient data 130B, the health care provider (HCP) data 130C, and the managed care data 130D, for example. The patient data 130B, health care provider (HCP) data 130C, and managed care data 130D may all be examples of data that represents control factors, which are factors other than the peer network that also influence the treating physician 215H's treatment decision. In the example of FIG. 3, the control factors may include patient factors (represented by the patient data 130B) and environmental factors (represented by the HCP data 130C and the managed care data 130D), as discussed in further detail herein.

The model 300 may comprise a deep learning engine comprises a Bidirectional Encoder Representations from Transformers (BERT) engine 305, deep neural networks (DNN) 310, and an activation function 315.

At block 605, the computing device 120 may use one or more DNNs to measure a magnitude of the set of environmental factors in the magnitude of control factor influence, wherein the set of environmental factors include a set of characteristics of the treating physician and a set of managed care factors. The DNN 310's function is to parse out the magnitude of the influence that environmental factors have in physician 215H's treatment decision. Stated differently, the DNN 310 allows the model 300 to control for environmental factors such as characteristics of the treating physician 215H (e.g., graduation year, board membership, years in practice, number of similar procedures they have done, etc.), prescribing preferences, promotions (e.g., promotional material sent to and face-to-face calls with treating physician 215H etc.), and demographics, for example (all of which may be derived from HCP data 130C). The DNN 310 may also allow the model 300 to control for environmental factors such as payer/plan copay rates, rejection, reversal, and copay differential (derived from managed care data 130D). For example, the DNN 310 may allow the model 300 to determine the influence on treating physician 215H's treatment decision of factors such as whether physician 215H is a prescribing doctor who can perform this treatment, whether the patient 205's healthcare plan allow for this kind of treatment, and whether there a rejection rate low enough that allows this treatment to be effective. The DNN 310 allows the model 300 to account for the magnitude of influence that environmental factors have on treating physician 215H's decision, and allows the model 300 to single out the influence of the peer network (which is also referred to as the causal influence) as discussed herein.

At block 610, the computing device 120 may use a bidirectional encoder representations from transformers (BERT) engine to measure a magnitude of the set of patient factors in the magnitude of control factor influence, the patient factors comprising sequential patient medical histories, demographic data. The BERT engine 305 may leverage a sequence model to train on patient longitudinal data (patient data 130B) such as patient sequential medical histories (indicating the effect of varying medical conditions among different patients), demographics, and medical/out of pocket treatment cost, for a large sample number of patients. In this way, the BERT engine 305 allows the model 300 to control for factors specific to the patient 205 (i.e., parse out the magnitude of influence that patient factors specific to patient 205 have on treating physician 215H's treatment decision). A patient's medical condition may be difficult to control for. This is because diagnosis and treatment often occur over months and years, some conditions advance over time, and there are tens of thousands of diagnosis codes. In addition, there can be millions of patient records. As a result, patient medical data can form a large and complex data structure with potentially tens of thousands of dimensions, which cannot be easily processed by the activation function 315. However, the BERT engine 305 may account for sequential information such as medical condition progress over time, and may project complex data structures with tens of thousands of dimensions into a smaller dimension space (e.g., from 10,000 dimensions to 200) via a process referred to as embedding.

When the BERT engine 305 projects a large and complex data (e.g., 10,000 dimensions) structure into a smaller dimension space, it may maintain the majority of the data from the 10,000 dimensions, thereby providing a dimension reduction mechanism. The BERT engine 305 allows the model 300 to account for the magnitude of influence that patient factors specific to patient 205 have on treating physician 215H's decision, and allows the model 300 to single out the influence of the peer network (which is also referred to as the causal influence) as discussed herein. The magnitude of the multi-relational network 400's influence (causal effect) may be derived from the multi-relational network data 320.

At block 615, activation function 315 may jointly model the magnitude of influence of the multi-relational network 400, the patient factors, and the environmental factors and allow the model 300 to measure the probability of the treatment decision made by the treating physician 215H based on all of these factors. As discussed herein, the major factor is multi-relational network data 320, while all other factors provide control. At block 620, the model 300 may output a treatment decision (e.g., treating physician 215H prescribed drug X), and the decomposition of what influenced the decision (e.g., 10% came from promotional material, 30% came from peer influence owing to multi-relational network 400). In some embodiments, an automation pipeline connects data from cloud storage 130 to optimize the efficiency of the model 300.

Referring back to FIG. 5, at block 515, computing device 120 may distribute the magnitude of peer influence among one or more physicians in the multi-relational network. Computing device 120 may utilize an influence attribution algorithm to perform a bottom up traversal analysis of the multi-relational network 400 and determine what portion of the peer influence magnitude should be assigned to each physician 215A-G at each level of the multi-relational network 400 through n-degrees of network separation to appropriately distribute the influence magnitude among physicians in the multi-relational network 400. The influence attribution algorithm may comprise a depth-first tree search algorithm, or any other appropriate algorithm. FIG. 4A illustrates the multi-relational network 400, with physicians 215A-H organized into a tree structure based on their respective links and corresponding influence weights (if applicable) and indicates the direction of influence (as opposed to influence credit) from top down with arrows pointing from physicians to the physicians that they influence. Treating physician 215H may be located at the bottom of the tree structure. In the example of FIG. 4A, physician A influences physicians B, C and D directly (and physicians F and H indirectly); both physicians C and D influence physician F directly (and physician H indirectly); and physician F directly influences physician H as indicated by the arrow pointing from physician F to physician H.

FIG. 4B illustrates the multi-relational network 400, illustrating the direction of influence credit with arrows pointing from physicians to the physicians who influence them and who will receive a portion of influence credit. Stated differently, FIG. 4B indicates the direction in which influence credit is distributed with arrows pointing from physicians who are influenced to physicians that influence them and are thus receiving a portion of the magnitude value of the influence of multi-relational network 400.

In response to physician H writing a prescription for drug X, the causal model 300 may decompose physician H's treatment decision to determine the magnitude of the influence of the multi-relational network 400 on the treatment decision as well as the magnitude of other control factors (e.g., managed care environment, HCP demographics, and promotional activities), as discussed herein. In order to distribute the magnitude of the influence of the multi-relational network 400, computing device 120 may utilize an influence attribution algorithm to determine how the magnitude of the influence of the multi-relational network 400 should be distributed among the physicians 215A-G in multi-relational network 400 as follows. More specifically, computing device 120 (executing the depth-first search algorithm) finds the physician that wrote the prescription, in this case physician 215H at the bottom of the tree and may calculate an influence score based on the magnitude of the influence of network 400 (using the output of the causal influence model 300). Computing device 120 may distribute the influence score to physicians 215 in the next level of the network 400 that influence physician 215H, based on their influence weight as determined by the computing device 120 when generating the multi-relational network 400. In the example of FIG. 4B, physician F is the only physician in the next level that influences physician H, and so the influence score may be distributed to physician F based on the weight of physician F's influence on physician H. Computing device 120 may then iterate this process until it reaches the top of the tree.

The computing device 120 may output the assigned score for each physician 215 in the network 400. Thus, each physician 215 may have a self-prescription score (determined as known in the art) and a peer influence score (determined using embodiments of the present disclosure). These scores may be combined to provide a total score (or may be used separately), which may allow a number of different analyses to be performed. For example, physicians 215 may be segmented into buckets (e.g., high, medium, low influence). In essence, by understanding their total values, the optimization of marketing strategies for each physician 215 can be performed. The techniques described herein may allow health care companies to gain insights of a physician 215's role in new product diffusion and enable brand teams to compare network values and tradeoff market research decisions (e.g., targeting, segmentation, multichannel marketing optimization, etc), for example.

Figure 7:
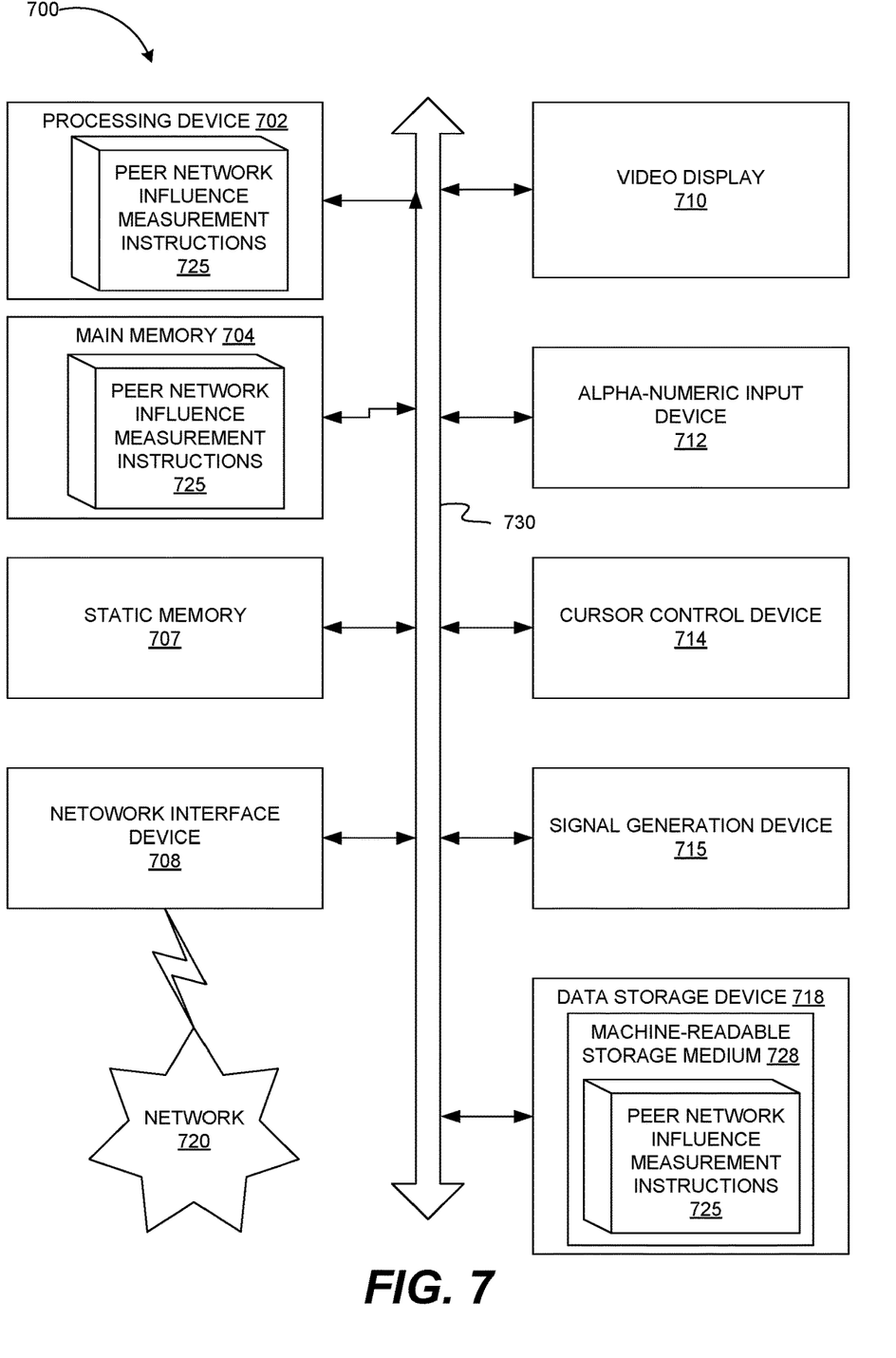
FIG. 7 is a block diagram of an example computing device that may perform one or more of the operations described herein, in accordance with some embodiments of the present disclosure.

FIG. 7 illustrates a diagrammatic representation of a machine in the example form of a computer system 700 within which a set of instructions, for causing the machine to perform any one or more of the methodologies discussed herein for determining which physicians in a peer network have the most peer influence is provided. The computer system 700 may generate a multi-relational network comprising links among a plurality of physicians based on peer network data, wherein each link indicates a first physician that influences a second physician, and a weight of the influence. The computer system 700 may additionally decompose, using a deep learning engine, a decision by a treating physician of the plurality of physicians into a magnitude of peer influence and a magnitude of control factor influence based on the multi-relational network and a plurality of control factors respectively, wherein the plurality of control factors includes a set of environmental factors and a set of patient factors. The computer system 700 may further distribute the magnitude of peer influence among one or more physicians in the multi-relational network based on the links each physician maintains with other physicians.

In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 700 may be representative of a server.

The exemplary computer system 700 includes a processing device 702, a main memory 704 (e.g., read-only memory (ROM), flash memory, dynamic random access memory (DRAM), a static memory 706 (e.g., flash memory, static random access memory (SRAM), etc.), and a data storage device 718, which communicate with each other via a bus 730. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 700 may further include a network interface device 708 which may communicate with a network 720. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 716 (e.g., a speaker). In one embodiment, video display unit 710, alphanumeric input device 712, and cursor control device 714 may be combined into a single component or device (e.g., an LCD touch screen).

Processing device 702 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute peer network influence measurement instructions 725, for performing the operations and steps discussed herein.

The data storage device 718 may include a machine-readable storage medium 728, on which is stored one or more sets of peer network influence measurement instructions 725 (e.g., software) embodying any one or more of the methodologies of functions described herein. The peer network influence measurement instructions 725 may also reside, completely or at least partially, within the main memory 704 or within the processing device 702 during execution thereof by the computer system 700; the main memory 704 and the processing device 702 also constituting machine-readable storage media. The peer network influence measurement instructions 725 may further be transmitted or received over a network 720 via the network interface device 708.

The machine-readable storage medium 728 may also be used to store instructions to provide peer network influence measurement to user-space applications, as described herein. While the machine-readable storage medium 728 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A method comprising:
generating a multi-relational network comprising links among a plurality of physicians based on peer network data, wherein each link indicates a first physician that influences a second physician, and a weight of the influence;
decomposing, using a deep learning engine, a treatment decision by a treating physician of the plurality of physicians into a magnitude of peer influence and a magnitude of control factor influence based on the multi-relational network and a plurality of control factors respectively, wherein the plurality of control factors includes a set of environmental factors and a set of patient factors, wherein decomposing the treatment decision comprises:
   measuring a magnitude of the set of environmental factors in the magnitude of control factor influence, and
   measuring a magnitude of the set of patient factors in the magnitude of control factor influence, wherein measuring the magnitude of the set of patient factors comprises:
      training a model of the deep learning engine with patient longitudinal data to identify patient factors that are likely to affect the treatment decision by the treating physician; and
      projecting, by an embedding process performed by the trained model of the deep learning engine, the set of patient factors from a first dimensional space into a second dimensional space, wherein the second dimensional space is smaller than the first dimensional space, and wherein the second dimensional space includes patient factors that are likely to affect the treatment decision by the treating physician;
distributing, by a processing device, the magnitude of peer influence among one or more physicians in the multi-relational network to determine a role that each of the one or more physicians in the multi-relational network has with respect to diffusion of information within the plurality of physicians; and
using the determined roles to optimize diffusion of products among the plurality of physicians in the multi-relational network.

2. The method of claim 1, wherein
the set of environmental factors include one or both of (i) a set of characteristics of the treating physician, or (ii) a set of managed care factors; and
wherein the set of patient factors include one or both of (i) patient medical histories, or (ii) patient demographic data.

3. The method of claim 1, wherein the trained model of the deep learning engine comprises a bidirectional encoder representations from transformers (BERT) engine configured perform the embedding process.

4. The method of claim 1, wherein a tree structure represents the multi-relational network and the treating physician is located at a lowest level of the tree structure.

5. The method of claim 4, wherein distributing the magnitude of peer influence among one or more physicians comprises:
calculating an influence score based on the magnitude of peer influence;
for each physician in a second level of the tree structure that influences the treating physician, distributing a portion of the influence score to the physician based on a weight of influence of the physician as indicated by the link between the physician and the treating physician; and
for each subsequent level of the tree structure, distributing a portion of the influence score to each physician in the subsequent level that influences one or more physicians in a previous level to whom a portion of the influence score was distributed based on a weight of influence of the physician as indicated by the link between the physician and the treating physician.

6. The method of claim 5, wherein distributing a portion of the influence score to a physician in a subsequent level that influences one or more physicians in a previous level comprises:
distributing a portion of the influence score based on a weight of influence of the physician on the one or more physicians in the previous level.

7. The method of claim 1, wherein generating the multi-relational network comprises:
identifying one or more missing links among the plurality of physicians; and
generating one or more link prediction models to complete the one or more missing links.

8. A system comprising:
a memory; and
a processing device, operatively coupled to the memory, the processing device configured to perform operations comprising:
   generating a multi-relational network comprising links among a plurality of physicians based on peer network data, wherein each link indicates a first physician that influences a second physician, and a weight of the influence;
   decomposing, using a deep learning engine, a treatment decision by a treating physician of the plurality of physicians into a magnitude of peer influence and a magnitude of control factor influence based on the multi-relational network and a plurality of control factors respectively, wherein the plurality of control factors includes a set of environmental factors and a set of patient factors, wherein decomposing the treatment decision comprises:
      measuring a magnitude of the set of environmental factors in the magnitude of control factor influence, and
      measuring a magnitude of the set of patient factors in the magnitude of control factor influence, wherein measuring the magnitude of the set of patient factors comprises:
         training a model of the deep learning engine with patient longitudinal data to identify patient factors that are likely to affect the treatment decision by the treating physician; and
         projecting, by an embedding process performed by trained model of the deep learning engine, the set of patient factors from a first dimensional space into a second dimensional space, the second dimensional space is smaller than the first dimensional space, wherein the second dimensional space includes patient factors that are likely to affect the treatment decision by the treating physician;
   distributing the magnitude of peer influence among one or more physicians in the multi-relational network to determine a role that each of the one or more physicians in the multi-relational network has with respect to diffusion of information within the plurality of physicians; and using the determined roles to optimize diffusion of products among the plurality of physicians in the multi-relational network.

9. The system of claim 8, wherein
the set of environmental factors include one or both of (i) a set of characteristics of the treating physician, or (ii) a set of managed care factors; and
wherein the set of patient factors includes one or both of (i) patient medical histories, or (ii) patient demographic data.

10. The system of claim 8, wherein the trained model of the deep learning engine comprises a bidirectional encoder representations from transformers (BERT) engine configured perform the embedding process.

11. The system of claim 8, wherein a tree structure represents the multi-relational network and the treating physician is located at a lowest level of the tree structure.

12. The system of claim 11, wherein distributing the magnitude of peer influence among one or more physicians comprises:
calculating an influence score based on the magnitude of peer influence; and
for each physician in a second level of the tree structure that influences the treating physician, distributing a portion of the influence score to the physician based on a weight of influence of the physician as indicated by the link between the physician and the treating physician; and
for each subsequent level of the tree structure, distributing a portion of the influence score to each physician in the subsequent level that influences one or more physicians in a previous level to whom a portion of the influence score was distributed based on a weight of influence of the physician as indicated by the link between the physician and the treating physician.

13. The system of claim 12, wherein distributing a portion of the influence score to an entity in a subsequent level that influences one or more entities in a previous level comprises:
distributing a portion of the influence score based on a weight of influence of the entity on the one or more physicians in the previous level.

14. The system of claim 8, wherein generating the multi-relational network comprises:
identifying one or more missing links among the plurality of physicians; and
generating one or more link prediction to complete the one or more missing links.

15. A non-transitory computer-readable medium having instructions stored thereon which, when executed by a processing device, cause the processing device to perform operations comprising:
generating a multi-relational network comprising links among a plurality of physicians based on peer network data, wherein each link indicates a first physician that influences a second physician, and a weight of the influence;
decomposing, using a deep learning engine, a treatment decision by a treating physician of the plurality of physicians into a magnitude of peer influence and a magnitude of control factor influence based on the multi-relational network and a plurality of control factors respectively, wherein the plurality of control factors includes a set of environmental factors and a set of patient factors, wherein decomposing the treatment decision comprises:
measuring a magnitude of the set of environmental factors in the magnitude of control factor influence,
measuring a magnitude of the set of patient factors in the magnitude of control factor influence, wherein measuring the magnitude of the set of patient factors comprises:
training a model of the deep learning engine with patient longitudinal data to identify patient factors that are likely to affect the treatment decision by the treating physician; and
projecting, by an embedding process performed by a trained model of the deep learning engine, the set of patient factors from a first dimensional space into a second dimensional space, the second dimensional space is smaller than the first dimensional space, wherein the second dimensional space includes patient factors that are likely to affect the treatment decision by the treating physician;
distributing, by the processing device, the magnitude of peer influence among one or more physicians in the multi-relational network to determine a role that each of the one or more physicians in the multi-relational network has with respect to diffusion of information within the plurality of physicians; and
using the determined roles to optimize diffusion of products among the plurality of physicians in the multi-relational network.

16. The non-transitory computer-readable medium of claim 15,
wherein the set of environmental factors include one or both of (i) a set of characteristics of the treating physician, or (ii) a set of managed care factors; and
wherein the set of patient factors include one or both of (i) patient medical histories, or (ii) patient demographic data.

17. The non-transitory computer-readable medium of claim 15, wherein the trained model of the deep learning engine comprises a bidirectional encoder representations from transformers (BERT) engine configured perform the embedding process.

18. The non-transitory computer-readable medium of claim 15, wherein a tree structure represents the multi-relational network and the treating physician is located at a lowest level of the tree structure.

19. The non-transitory computer-readable medium of claim 18, wherein distributing the magnitude of peer influence among one or more physicians comprises:
calculating an influence score based on the magnitude of peer influence; and
for each physician in a second level of the tree structure that influences the treating physician, distributing a portion of the influence score to the physician based on a weight of influence of the physician as indicated by the link between the physician and the treating physician; and
for each subsequent level of the tree structure, distributing a portion of the influence score to each physician in the subsequent level that influences one or more physicians in a previous level to whom a portion of the influence score was distributed based on a weight of influence of the physician as indicated by the link between the physician and the treating physician.

20. The non-transitory computer-readable medium of claim 19, distributing a portion of the influence score to a physician in a subsequent level that influences one or more physicians in a previous level comprises:
   distributing a portion of the influence score based on a weight of influence of the physician on the one or more physicians in the previous level.

\* \* \* \* \*

UNITED STATES PATENT AND TRADEMARK OFFICE
CERTIFICATE OF CORRECTION

PATENT NO. : 11,923,074 B2
APPLICATION NO. : 17/174705
DATED : March 5, 2024
INVENTOR(S) : Ruoxin Li et al.

It is certified that error appears in the above-identified patent and that said Letters Patent is hereby corrected as shown below:

In the Claims

Column 17, Line 33, Claim 1 – delete "space," and insert -- space; --.

Column 19, Line 18, Claim 10 – before "perform" insert -- to --.

Column 20, Line 44, Claim 17 – before "perform" insert -- to --.

Signed and Sealed this
Fourteenth Day of May, 2024

Katherine Kelly Vidal
*Director of the United States Patent and Trademark Office*